US008815782B2

(12) United States Patent
Zeiner et al.

(10) Patent No.: US 8,815,782 B2
(45) Date of Patent: Aug. 26, 2014

(54) USE OF DNAZYMES FOR ANALYSIS OF AN RNA SAMPLE

(71) Applicant: Agilent Technologies, Inc., Loveland, CO (US)

(72) Inventors: Gusti Zeiner, San Mateo, CA (US); Robert A. Ach, San Francisco, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 6 days.

(21) Appl. No.: 13/666,752

(22) Filed: Nov. 1, 2012

(65) Prior Publication Data

US 2013/0123129 A1    May 16, 2013

Related U.S. Application Data

(60) Provisional application No. 61/558,935, filed on Nov. 11, 2011.

(51) Int. Cl.
    *C40B 50/06* (2006.01)
(52) U.S. Cl.
    USPC .......................................................... 506/25
(58) Field of Classification Search
    None
    See application file for complete search history.

(56) References Cited

PUBLICATIONS

Hengesbach et al (2008) "Use of DNAzymes for site-specific analysis of ribonucleotide modifications" RNA 14:180-187.*
Schutz, et al. "Capture and sequence analysis of RNAs with terminal 29,39-cyclic phosphates." RNA (2010), 16:621-31.
Roy, et al., "Sequence-specific cleavage of hepatitis C virus RNA by DNAzymes: inhibition of viral RNA translation and replication", J Gen Virol, 2008, 89:1579-86.
Santoro, et al., "A general purpose RNA-cleaving DNA enzyme", Proc Natl Acad Sci, 1997, 94:4262-6.
Schlosser, et al., "In vitro selection of small RNA-cleaving deoxyribozymes that cleave pyrimidine-pyrimidine junctions", Nucleic Acids Res, 2008, 36:4768-77.
Silverman, et al., "In vitro selection, characterization, and application of deoxyribozymes that cleave RNA", Nucleic Acids Res, 2005, 33:6151-63.

* cited by examiner

*Primary Examiner* — Tracy Vivlemore
*Assistant Examiner* — Karen S Weiler

(57) ABSTRACT

Provided herein is method comprising: contacting an initial RNA sample containing a population of different RNA molecules with a divalent cation and a set of DNAzymes that are designed to cleave multiple target RNAs in the initial sample, thereby producing a product RNA sample that comprises: a) uncleaved RNA molecules and b) cleaved RNA fragments that contain a 2',3'-cyclic-phosphate and a 5' hydroxyl as the result of DNAzyme cleavage.

17 Claims, 4 Drawing Sheets

US 8,815,782 B2

SEQUENCE LISTING

```
<160> NUMBER OF SEQ ID NOS: 1

<210> SEQ ID NO 1
<211> LENGTH: 15
<212> TYPE: DNA
<213> ORGANISM: Artificial sequence
<220> FEATURE:
<223> OTHER INFORMATION: Synthetic oligonucleotide
```

```
<400> SEQUENCE: 1
ggctagctac aacga                                                    15
```

USE OF DNAZYMES FOR ANALYSIS OF AN RNA SAMPLE

Two of the key challenges for nucleic acid-based clinical diagnostics are sensitivity and specificity, particular when interrogating highly complex samples such as whole-blood or saliva for the presence of circulating cancer or pathogens. In these complex samples, the nucleic acids of interest are often obscured by a vast excess of host DNA and RNA that are of little clinical interest.

SUMMARY

Provided herein is method comprising: contacting an initial RNA sample containing a population of different RNA molecules with a divalent cation and a set of DNAzymes that are designed to cleave multiple target RNAs in the initial sample, thereby producing a product RNA sample that comprises: a) uncleaved RNA molecules and b) cleaved RNA fragments that contain a 2',3'-cyclic-phosphate and a 5' hydroxyl as the result of DNAzyme cleavage. In certain embodiments, the method may further comprise ligating a first adaptor onto the 3' ends of at least some of said cleaved RNA fragments using a 2',3'-cyclic phosphate-specific ligase (e.g., using a eukarytic tRNA ligase or an RtcB ligase). These ligation products may be directly hybridized to an array (e.g., if the first adaptor is labeled) or purified away from other products in the same (e.g., if the first adaptor has an affinity tag). Alternatively, the ligated 3' adaptor may contain a RNA polymerase promoter that after first- and second-strand cDNA synthesis, may be used to direct transcription of the adaptor-ligated RNAs; these transcribed RNAs can be labeled with fluorescent dyes during transcription and the sample can be hybridized to a microarray to detect the amplified, labeled RNA molecules. In other embodiments, the initial RNA sample that is contacted may contain adaptor-ligated RNA molecules that have a 3' adaptor and a 5' adaptor. In these embodiments, product RNA sample may be reverse transcribed and amplified by PCR. Only the uncleaved samples should be amplified.

DEFINITIONS

Figure 1:
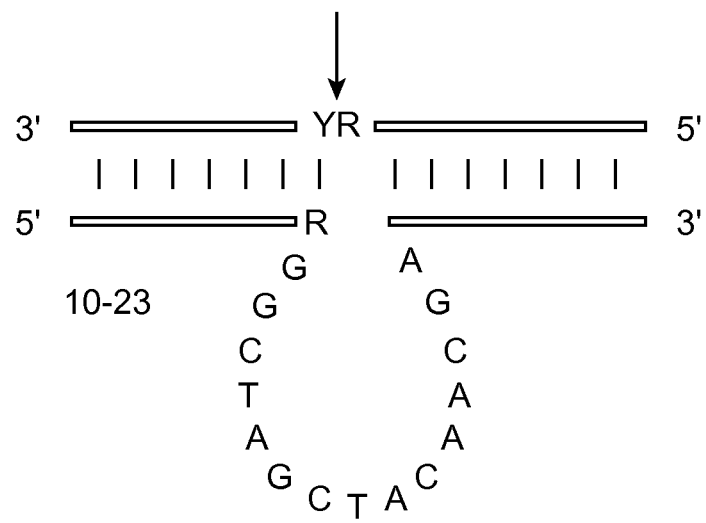
FIG. 1 schematically illustrates an exemplary 10-23 DNAzyme (SEQ ID NO: 1).

The term "RNA sample", as used herein, relates to a mixture of materials, typically, although not necessarily, in liquid form, containing one or more RNA molecules. An RNA sample may be obtained from cells, e.g., mammalian cells, for example. An RNA sample may contain a population of different RNA molecules, in which case it may contain more than 1,000, more than 10,000, more than 50,000, or more than 100,000 up to 1M or more different species of RNA, i.e., RNA molecules of different sequence. An RNA sample may contain long RNA molecules, which are RNA molecules that are at least 50 nt in length. Long RNA molecules include mRNA molecules, rRNA molecules, tRNA molecules, pre-miRNAs, snRNAs and long non-coding RNA molecules such as large intergenic RNA (lincRNA) molecules. Some long RNA molecules may be in the range of 50 to 10 kb in length, e.g., 200 nt to 10 kb in length. An RNA sample may also contain short RNA molecules which are RNA molecules that are below 50 nt in length. Short RNA molecules a variety of small non-coding regulatory RNAs that may be generically referred herein to as "small RNAs", i.e, short interfering RNAs, microRNAs, tiny non-coding RNAs piwi-interacting small RNAs (piRNAs) and small modulatory RNAs.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated purines or pyrimidines, halogenated purines or pyrimidines, deaza-purines or pyrimidines or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, such as but not limited to MOE, LNA or the likes. Nucleotides may include those that when incorporated into an extending strand of a nucleic acid enables continued extension (non-chain terminating nucleotides) and those that prevent subsequent extension (e.g. chain terminators).

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally occurring nucleotides include guanine, cytosine, adenine, thymine and uridine (G, C, A T and U, respectively).

The terms "ribonucleic acid" and "RNA" as used herein mean a polymer composed of ribonucleotides.

The terms "deoxyribonucleic acid" and "DNA" as used herein mean a polymer composed of deoxyribonucleotides.

"Isolated" or "purified" generally refers to isolation of a substance (compound, polynucleotide, protein, polypeptide, polypeptide composition) such that the substance comprises a significant percent (e.g., greater than 1%, greater than 2%, greater than 5%, greater than 10%, greater than 20%, greater than 50%, or more, usually up to about 90%-100%) of the sample in which it resides. In certain embodiments, a substantially purified component comprises at least 50%, 80%-85%, or 90-95% of the sample. Techniques for purifying polynucleotides and polypeptides of interest are well-known in the art and include, for example, ion-exchange chromatography, affinity chromatography and sedimentation according to density. Generally, a substance is purified when it exists in a sample in an amount, relative to other components of the sample, that is not found naturally.

The term "oligonucleotide", as used herein, denotes a single-stranded multimer of nucleotides from about 2 to 500 nucleotides, e.g., 2 to 200 nucleotides. Oligonucleotides may be synthetic or may be made enzymatically, and, in some embodiments, are 4 to 50 nucleotides in length. Oligonucleotides may contain ribonucleotide monomers (i.e., may be RNA oligonucleotides) or deoxyribonucleotide monomers, or both ribonucleotide monomers and deoxyribonucleotide monomers and may additionally comprise non-natural or modified nucleotide monomers. Oligonucleotides may be 5 to 20, 11 to 30, 31 to 40, 41 to 50, 51-60, 61 to 70, 71 to 80, 80 to 100, 100 to 150 or 150 to 200, up to 500 nucleotides in length, for example. An oligonucleotide may be labeled or unlabeled.

The term "label", as used herein, in the context of a labeled oligonucleotide (e.g., a labeled adaptor) refers to moiety via which an oligonucleotide can be detected or purified. Mass tags, fluorescent tags, and chemiluminescent tags are examples of labels, as are nucleosides harboring radioactive phosphorous, sulfur or hydrogen.

As used herein, the term "affinity tag" refers to a member of a specific binding pair, i.e. two molecules where one of the molecules through chemical or physical means specifically binds to the other molecule. The complementary member of the specific binding pair may be immobilized (e.g., to a chromatography support, a bead or a planar surface) to produce an affinity chromatography support that specifically binds the affinity agent. Tagging a compound of interest with an affinity agent allows the compound to be separated from a mixture of untagged compounds using affinity chromatography. Two complementary polynucleotide sequences and biotin and streptavidin can be a specific binding pairs. The specific binding pairs may include analogs, derivatives and fragments of the original specific binding member. For example, an antibody directed to a protein antigen may also recognize peptide fragments, chemically synthesized peptidomimetics, labeled protein, derivatized protein, etc., so long as an epitope is present.

As used herein, the term "biotin moiety" refers to an affinity agent that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least $10^{-8}$M. A biotin affinity agent may also include a linker, e.g., -LC-biotin, -LC-LC-Biotin, -SLC-Biotin or -PEG$_n$-Biotin where n is 3-12.

The term "duplex" or "double-stranded" as used herein refers to nucleic acids formed by hybridization of two single strands of nucleic acids containing complementary sequences. In most cases, genomic DNA is double-stranded.

The term "complementary" as used herein refers to a nucleotide sequence that base-pairs by non-covalent bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotide is complementary to every nucleotide in the target nucleic acid in all the corresponding positions.

The term "probe," as used herein, refers to a nucleic acid that is complementary to a nucleotide sequence of interest. In certain cases, detection of a target analyte requires hybridization of a probe to the target. In certain embodiments, a probe may be surface-tethered, i.e., immobilized on a surface of a substrate, where the substrate can have a variety of configurations, e.g., a sheet, bead, or other structure. In certain embodiments, a probe may be present on a surface of a planar support, e.g., in the form of an array.

The phrase "surface-bound nucleic acid" refers to a nucleic acid that is immobilized on a surface of a solid substrate, where the substrate can have a variety of configurations, e.g., a sheet, bead, or other structure. In certain embodiments, the nucleic acid probes employed herein are present on a surface of the same planar support, e.g., in the form of an array.

The phrase "labeled population of nucleic acids" refers to mixture of nucleic acids that are detectably labeled, e.g., fluorescently labeled or labeled with other detectable molecular tags, such that the presence of the nucleic acids can be detected by assessing the presence of the label.

The term "array" encompasses the term "microarray" and refers to an ordered array presented for binding to nucleic acids and the like.

An "array," includes any two-dimensional or three-dimensional arrangement of addressable regions, e.g., spatially addressable regions or optically addressable regions, bearing nucleic acids, particularly oligonucleotides or synthetic mimetics thereof, and the like. In some cases, the addressable regions of the array may not be physically connected to one another, for example, a plurality of beads that are distinguishable by optical or other means may constitute an array. Where the arrays are arrays of nucleic acids, the nucleic acids may be adsorbed, physisorbed, chemisorbed, or covalently attached to the arrays at any point or points along the nucleic acid chain.

Any given substrate may carry one, two, four or more arrays disposed on a surface of the substrate. Depending upon the use, any or all of the arrays may be the same or different from one another and each may contain multiple spots or features. An array may contain one or more, including more than two, more than ten, more than one hundred, more than one thousand, more ten thousand features, or even more than one hundred thousand features, in an area of less than 20 cm$^2$ or even less than 10 cm$^2$, e.g., less than about 5 cm$^2$, including less than about 1 cm$^2$, less than about 1 mm$^2$, e.g., 100 μm$^2$, or even smaller. For example, features may have widths (that is, diameter, for a round spot) in the range from a 5 μm to 1.0 cm. In other embodiments each feature may have a width in the range of 1.0 μm to 1.0 mm, usually 5.0 μm to 500 and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, photolithographic array fabrication processes are used. It will be appreciated though, that the inter-feature areas, when present, could be of various sizes and configurations.

Each array may cover an area of less than 200 cm$^2$, or even less than 50 cm$^2$, 5 cm$^2$, 1 Cm$^2$, 0.5 cm$^2$, or 0.1 cm$^2$. In certain embodiments, the substrate carrying the one or more arrays will be shaped generally as a rectangular solid (although other shapes are possible), having a length of more than 4 mm and less than 150 mm, usually more than 4 mm and less than 80 mm, more usually less than 20 mm; a width of more than 4 mm and less than 150 mm, usually less than 80 mm and more usually less than 20 mm; and a thickness of more than 0.01 mm and less than 5.0 mm, usually more than 0.1 mm and less than 2 mm and more usually more than 0.2 mm and less than 1.5 mm, such as more than about 0.8 mm and less than about 1.2 mm.

Arrays can be fabricated using drop deposition from pulse-jets of either precursor units (such as nucleotide or amino acid monomers) in the case of in situ fabrication, or the previously obtained nucleic acid. Such methods are described in detail in, for example, the previously cited references including U.S. Pat. Nos. 6,242,266, 6,232,072, 6,180,351, 6,171,797, 6,323,043, U.S. Patent Application Publication No. 20040203138 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used. Inter-feature areas need not be present particularly when the arrays are made by photolithographic methods as described in those patents.

Arrays may also be made by distributing pre-synthesized nucleic acids linked to beads, also termed microspheres, onto a solid support. In certain embodiments, unique optical signatures are incorporated into the beads, e.g. fluorescent dyes, that could be used to identify the chemical functionality on any particular bead. Since the beads are first coded with an optical signature, the array may be decoded later, such that correlation of the location of an individual site on the array with the probe at that particular site may be made after the array has been made. Such methods are described in detail in, for example, U.S. Pat. Nos. 6,355,431, 7,033,754, and 7,060,431.

An array is "addressable" when it has multiple regions of different moieties (e.g., different oligonucleotide sequences) such that a region (i.e., a "feature" or "spot" of the array) at a particular predetermined location (i.e., an "address") on the array contains a particular sequence. Array features are typically, but need not be, separated by intervening spaces. An array is also "addressable" if the features of the array each have an optically detectable signature that identifies the moiety present at that feature. An array is also "addressable" if the features of the array each have a signature, which is detectable by non-optical means, that identifies the moiety present at that feature.

The terms "determining", "measuring", "evaluating", "assessing", "analyzing", and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

As used herein, the term "$T_m$" refers to the melting temperature of an oligonucleotide duplex at which half of the duplexes remain hybridized and half of the duplexes dissociate into single strands. The $T_m$ of an oligonucleotide duplex may be experimentally determined or predicted using the following formula $T_m=81.5+16.6(\log_{10}[Na^+])+0.41$ (fraction G+C)−(60/N), where N is the chain length and $[Na^+]$ is less than 1 M. See Sambrook and Russell (2001; Molecular Cloning: A Laboratory Manual, $3^{rd}$ ed., Cold Spring Harbor Press, Cold Spring Harbor N.Y., ch. 10). Other more advanced models that depend on various parameters may also be used to predict $T_m$ of oligonucleotide duplexes may also be used depending on various hybridization conditions.

As used herein, the term "$T_m$-matched" refers to a plurality of nucleic acid duplexes having $T_m$s that are within a defined range, e.g. ±5° C., ±10° C., or ±15° C.

The term "hybridization conditions" as used herein refers to hybridization conditions that are sufficient to anneal an oligonucleotide of a sufficient length to a probe that is complementary to a nucleotide sequence of the probe. The hybridization conditions provide for dissociation of duplexes that anneal over a short length of region (e.g. less than 50, less than 40, less than 30, or less than 20 contiguous nucleotides). Such conditions may differ from one experiment to the next depending on the length and the nucleotide content of the complementary region. In certain cases, the temperature for low-stringency hybridization may be 5°-10° C. lower than the calculated Tm of the resulting duplex under the conditions used.

The term "stringent assay conditions" as used herein refers to conditions that are compatible to produce binding pairs of nucleic acids, e.g., probes and targets, of sufficient complementarity to provide for the desired level of specificity in the assay while being incompatible to the formation of binding pairs between binding members of insufficient complementarity to provide for the desired specificity. The term stringent assay conditions refers to the combination of hybridization and wash conditions.

The term "mixture", as used herein, refers to a heterogeneous combination of elements, that are interspersed and not in any particular order. A mixture is heterogeneous and not spatially separable into its different constituents. Examples of mixtures of elements include a number of different elements that are dissolved in the same aqueous solution, or a number of different elements attached to a solid support at random or in no particular order in which the different elements are not spatially distinct. In other words, a mixture is not addressable. To be specific, an array of surface-bound oligonucleotides, as is commonly known in the art and described below, is not a mixture of surface-bound oligonucleotides because the species of surface-bound oligonucleotides are spatially distinct and the array is addressable.

As used herein, the term "data" refers to refers to a collection of organized information, generally derived from results of experiments in lab or in silico, other data available to one of skilled in the art, or a set of premises. Data may be in the form of numbers, words, annotations, or images, as measurements or observations of a set of variables. Data can be stored in various forms of electronic media as well as obtained from auxiliary databases.

If a nucleic acid probe "corresponds to" or is "for" a certain RNA, the nucleic acid probe base pairs with, i.e., specifically hybridizes to, that RNA. As will be discussed in greater detail below, a nucleic acid probe for a particular RNA and the particular RNA, or complement thereof, contains at least one region of contiguous nucleotides that is identical in sequence.

As used herein, the terms "multiple", "set of", "population of" and "plurality" are used interchangeably to refer to more than 1, including at least 2, at least 10, at least 100, at least 1,000, at least 5,000, at least 10,000, at least 50,000, at least 100,000, at least 500,000 or up to at least 1M or more.

As used herein, the term "total cellular RNA" is an RNA sample that contains at least tRNA, rRNA, mRNA, lincRNA and small RNA.

As used herein, the term "depleted", in the context of a total cellular RNA sample that has been depleted for tRNA, rRNA, or another type of RNA, is total cellular RNA sample from which tRNA, rRNA, or another type of RNA has been subtracted, i.e., removed. Depletion may be done by subtraction (i.e., by removing RNAs hybridization), enzymatically (e.g., using RNaseH, or by DNAzyme-mediated cleavage) or by blocking (e.g., by blocking the action of an enzyme such as reverse transcriptase by annealing an oligo in its path to block it), for example.

As used herein, the term "initial RNA sample" is an RNA sample that has not been exposed to a DNAzyme and that contains uncleaved RNA molecules. Such a sample may contain, for example, total cellular RNA or a total cellular RNA that has been depleted for rRNA and/or tRNA, or another type of RNA. An initial RNA sample contains at least one type of intact long RNA and one type of short RNA. An initial RNA sample may itself contain fragmented RNA, produced from an earlier sample in way that does not produce an 2',3' cyclic phosphate end.

As used herein, the terms "product RNA sample" and "fragmented RNA sample" refer to a sample that contains fragments of RNA. A fragmented RNA sample can made from an initial RNA sample by exposing the initial RNA sample to a set of DNAzymes, or by heating an RNA sample in the presence of a metal ion.

As used herein, the term "fragmented RNA molecules" refer to RNA fragments that are obtained by fragmentation of RNA. Depending on how fragmentation is done, fragments of RNA molecules may have a 2',3' cyclic phosphate group at the 3' terminus.

As used herein, the term "fragmentation conditions" refer to an environment or an agent that induces fragmentation of RNA.

As used herein, the term "adaptor" refers to an oligonucleotide or single nucleotide that is ligatable onto another nucleic acid. An adaptor may be, e.g., an RNA adaptor, a DNA adaptor, or it may be composed of both ribonucleotides and deoxyribonucleotides or analogs thereof. An adaptor may be labeled or unlabeled and in certain cases may be of 2-50 bases, e.g., 6 to 12 bases, in length or longer depending on the application. An adaptor may contain an affinity tag. Single nucleotide pNp-dye conjugates (e.g., as described in Wang et al, RNA 2007 13: 151-159) are also considered adaptors for the purposes of this disclosure.

As used herein, the terms "5'-OH" and "5'-hydroxyl" refers to a nucleotide at the 5' terminus of a nucleic acid, where the nucleotide has a hydroxyl group at the 5' position.

As used herein, the terms "3'-OH" and "3'-hydroxyl" refers to a nucleotide at the 3' terminus of a nucleic acid, where the nucleotide has a hydroxyl group at the 3' position.

As used herein, the term "3'-P" or "3'-phosphate" refers to a nucleotide at the 3' terminus of a nucleic acid, where the nucleotide has a phosphate group at the 3' position.

As used herein, the term "5'-P" or "5'-phosphate" refers to a nucleotide at the 5' terminus of a nucleic acid, where the nucleotide has a phosphate group at the 5' position.

As used herein, the terms "2'-OH and 3'-PO" and "2'-hydroxyl and 3'-phosphate", in the context of a 3' terminus, refers to a nucleotide at the 3' terminus of a nucleic acid, where the sugar moiety of the nucleotide has both a phosphate group at the 3' position and a hydroxyl group at the 2' position.

As used herein, the term "2',3'-cyclic phosphate", in the context of a 3' terminus comprising 2',3'-cyclic phosphate, refers to a nucleotide at the 3' terminus of a nucleic acid, where the sugar moiety of the nucleotide has a phosphate group connected to the 2' and 3' positions, as shown below:

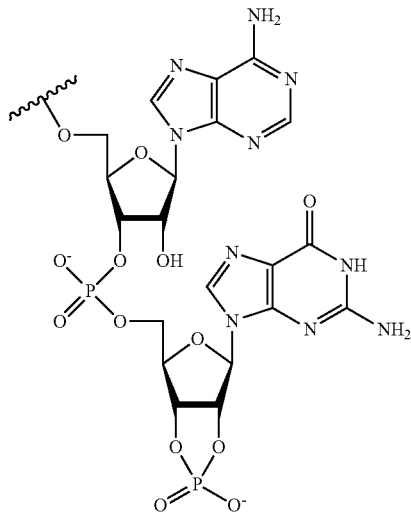

As used herein, the term "2',3'-cyclic phosphate-specific ligase" refers to any enzyme that can ligate a 3' terminus containing a 2',3'-cyclic phosphate group to the 5' end of another nucleic acid. Such enzymes include eukaryotic tRNA ligases and RtcB ligase, as discussed below.

As used herein, the term "eukaryotic tRNA ligase" refers to a multifunctional enzyme that has: a) a ligase activity that catalyzes ligation of the 5' terminus of a nucleic acid having a 5'-phosphate to the 3' terminus of a nucleic acid having a 3' terminus having a 2'-phosphate and a 3'-hydroxyl to produce a ligation product that contains a 2' phosphate at the site of ligation and b) a cyclic phosphodiesterase (CPD) activity that catalyzes the hydrolysis of a 2',3'-cyclic phosphate group to produce a 2'-phosphate and 3'-hydroxyl; and, optionally, c) a kinase activity that catalyzes the phosphorylation of a 5'-hydroxyl to produce a 5'-phosphate. Wild type tRNA ligase enzymes have all three activities and are arranged as follows: a N-terminal ligase module, a central kinase module and a C-terminal 2',3'-cyclic phosphodiesterase module. The term "eukaryotic tRNA ligase" explicitly encompasses a single polypeptide having ligase and phosphodiesterase domains, as well as two polypeptides, one having ligase activity and the other having phosphodiesterase activity.

As used herein, the term "RtcB ligase" refers to any enzyme that has the ability to catalyze the ligation of the 3' end of an RNA having a 3' terminal 2',3'-cyclic phosphate to the 5' end of an RNA having a 5'-hydroxyl. Several examples of such enzymes (which are generically but not always referred to as "RtcB" protein in the art), are known in bacteria, archaea and eukarya (particularly in metazoan and protozoa species but not in some fungi and plants). RtcB ligases are structurally unrelated to 3'-OH RNA ligases, which ligate a 5'-phosphate-containing RNA to a 3'-hydroxyl-containing RNA, rather than ligating a 5'-hydroxyl-containing RNA to a 3' terminal 2',3'-cyclic phosphate-containing RNA. Additionally, RtcB ligases are structurally unrelated to the afore mentioned eukaryotic tRNA ligases. The structure, function, biochemical features and phylogenetic distribution of various RtcB ligases are described in a variety of publications, including: Tanaka et al (*RtcB is the RNA ligase component of an Escherichia coli RNA repair operon.* J. Biol. Chem. Jan. 11, 2011, e-pub ahead of print), Englert et al (*Archaeal 3'-phosphate RNA splicing ligase characterization identifies the missing component in tRNA maturation*. Proc. Natl. Acad. Sci. 2011 108: 2-7), and Okada et al (*Crystal structure of an RtcB homolog protein (PH1602-extein protein) from Pyrococcus horikoshii reveals a novel fold*. Proteins 2006 63: 1084-6), Popow et al (*HSPC117 Is the Essential Subunit of a Human tRNA Splicing Ligase Complex*) Science 331, no. 6018 (2011): 760.

As used herein, the term "DNAzyme" refers any DNA that can catalytic cleave the phosphodiester bond in an RNA in the presence of a divalent cation (e.g., $Mg^2$) to produce a product that contains a 3' terminus comprising a 2',3'-cyclic phosphate and a 5' terminal hydroxyl. Structurally, DNAzymes contain a two "feet" that hybridize to a target sequence and are separated by a domain which can be a single-stranded loop (see, e.g., FIG. 1) or a partially base-paired hairpin. DNAzymes are extensively reviewed in, e.g., Baum et al (Cell Mol. Life. Sci. 2008 65:2156-74), Schlosser et al (Chem. Biol. 2009 16:311-22), Pan et al (Expert Opin. Biol. Ther. 2008 8:1071-85), Chan et al (Intern. Med. J. 2009 39:249-51) and Cairns et al (Cum Drug Targets. 2002 3:269-79), which are incorporated by reference for their description of different types of DNAzyme. Several types of DNAzyme are known (e.g., 10-23 and 8-17 enzymes), and new types of DNAzymes are readily made using known in vitro evolution methods, see, e.g., Santoro et al (Proc. Natl. Acad. Sci. 1997 94:4262-6), Santoro et al (J. Am. Chem. Soc. 2000 22 122:2433-9), Schlosserl Nucleic Acids Res. 2009 February; 37(2): 413-420. Joyce et al (Angew Chem. Int. Ed. Engl. 2007 46: 6420-36); Joyce et al (Annu. Rev. Biochem. 2004 73: 791-836), Wilson et al (Annu. Rev. Biochem. 1999 68: 611-47) and Santoro et al (Biochemistry. 1998 37:13330-4), which are incorporated by reference herein.

As used herein, the term "10-23 DNAzyme" refers any DNAzyme that contains a) a 15 nucleotide loop structure that has up to 1 nucleotide substitution relative to the loop shown in FIG. 1 and b) two feet that vary in length (e.g. of 7 to 20 nucleotides) and sequence depending on the target, and c) a purine residue at the 3' end of the 5' foot. 10-23 DNAzymes cleave the phosphoester bond between an unpaired pyramidine and an adjacent purine residue. An exemplary 10-23 DNAzyme is shown in FIG. 1.

DESCRIPTION OF EXEMPLARY EMBODIMENTS

Before the present invention is described in greater detail, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Several steps in the method described below, e.g., cDNA synthesis, amplification by PCR, DNA sequencing, etc., are known and may be readily adapted from those described in Ausubel, et al, (Short Protocols in Molecular Biology, 3rd ed., Wiley & Sons, 2002) and Sambrook, et al, (Molecular Cloning: A Laboratory Manual, Third Edition, (2001) Cold Spring Harbor, N.Y.), as well as a variety of other sources.

Figure 2:
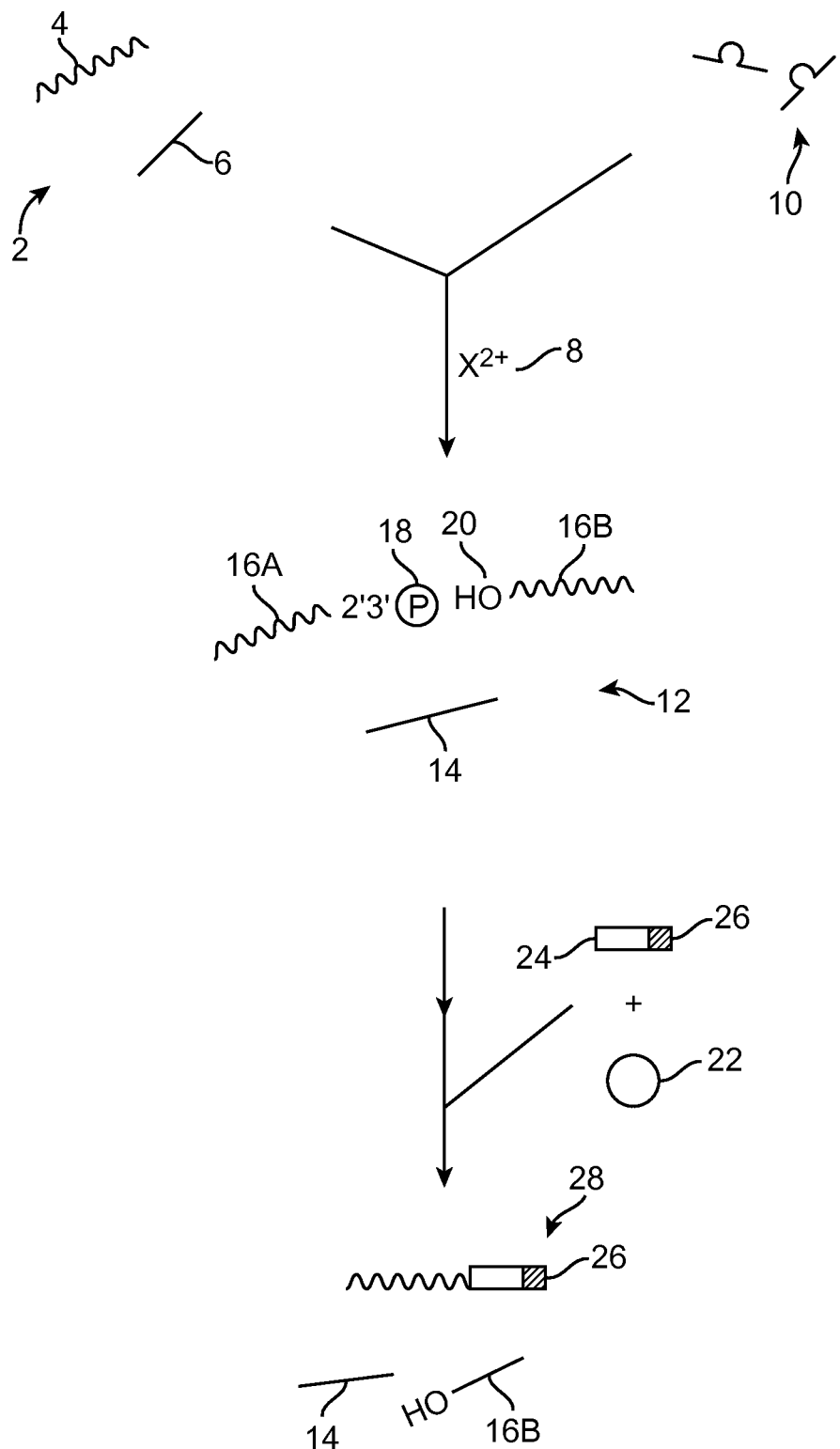
FIG. 2 schematically illustrates an embodiment of the method.

With reference to FIG. 2, one embodiment of the method may comprise: contacting an initial RNA sample 2 containing a population of different RNA molecules (as shown RNA molecules 4 and 6) with a divalent cation 8 (e.g., $Mg^{2+}$, $Zn^{2+}$ or $Mn^{2+}$) and a set of DNAzymes 10 that are designed to cleave multiple target RNAs in the initial sample, thereby producing a product RNA sample 12 that comprises: a) uncleaved RNA molecules 14 and b) cleaved RNA fragments 16A and 16B that contain a 2',3'-cyclic-phosphate 18 and a 5' hydroxyl 20 as the result of DNAzyme cleavage. As noted above, the DNAzyme may be a 10-23 DNAzyme, although any other DNAzyme that can site-specifically cleave RNA to produce a 2',3'-cyclic-phosphate may be employed. In particular cases, the contacting may involve cycling the reaction through denaturation and renaturation temperatures (where denaturation may occur at a temperature of least 60° C., e.g., 80° C. to 90° C.) and renaturation may occur at a temperature of less than 50° C., e.g., at about 30° C. to 42° C.) to maximize cleavage by the DNAzyme. The set of DNAzymes may comprise at least 10 different DNAzymes (e.g., at least 100, at least 500, at least 1,000, at least 10,000, at least 50,000 up to 100,000 or more) that specifically target different RNAs (e.g., at least 10, at least 100, at least 500, at least 1,000, at least 10,000, up to 50,000 or more different species of target RNA). In certain embodiments, a single species of target RNA may be targeted by up to 100 different DNAzymes, in which case the DNAzymes may be spaced along a target RNA by, e.g., 50-500 nt. In some embodiments, a single species of target RNA may by targeted by less then 5 (e.g., only one or two) DNAzymes. In certain cases the DNAzymes are specific in that they do not cross-hybridize to non-target sequences in the same sample. In other embodiments, the DNAzymes may be non-specific in that they specifically target several different RNAs via a sequence that is shared in the different RNAs.

The DNAzymes used may be made separately and then combined in the reaction. In other embodiments, DNAzymes may be synthesized on a solid support in an array, where the nucleotide sequences defining the DNAzymes are grown in situ. Oligonucleotide arrays can be fabricated using any means, including drop deposition from pulse jets or from fluid-filled tips, etc, or using photolithographic means. Polynucleotide precursor units (such as nucleotide monomers), in the case of in situ fabrication can be deposited. Oligonucleotides synthesized on a solid support may then be cleaved off to generate a library of oligonucleotides. Such methods are described in detail in, for example U.S. Pat. Nos. 7,385,050, 6,222,030, 6,323,043, and US Pat Pub No. 2002/0058802, etc., the disclosures of which are herein incorporated by reference. The oligos may be tethered to a solid support via a cleavable linker, and cleaved from the support before use.

The method summarized above may be employed to deplete an RNA sample (e.g., a sample containing total RNA) of potential interfering RNAs (e.g., high abundance RNAs such as rRNAs and rRNAs) or to select RNAs of interest (e.g., a set of particular mRNAs) from an RNA sample (e.g., a sample containing total RNA), methods for which are described in greater detail below. The DNAzymes used in the method may target: mRNA molecules, rRNA molecules, tRNA molecules, pre-miRNAs, snRNAs, long non-coding RNA molecules such as large intergenic RNA (lincRNA) molecules or small RNAs, i.e, short interfering RNAs, microRNAs, tiny non-coding RNAs piwi-interacting small RNAs (piRNAs) and small modulatory RNAs, or any combination of the same.

In one exemplary embodiment, the interfering RNA may be cleaved into small products (e.g., in the size range of 30-100 nucleotides in length), and the non-cleaved products may be separated from the cleaved products by size (e.g., by size exclusion). For example, the product can be size-fractionated by passage through a spin-column (such as a G50 sephadex column or a Qiaquick column), whereby RNA fragments are removed.

In another embodiment, after DNAzyme treatment, the method may further comprise ligating a first adaptor onto the 3' ends of at least some of the cleaved RNA fragments using a 2',3'-cyclic phosphate-specific ligase, thereby producing a ligated sample containing ligation products. This step of the method may be done in a variety of different ways depending on the chosen enzyme and the desired outcome. In particular embodiments, a eukarytic tRNA ligase may be used, in which case the first adaptor should have a 5'-phosphate or 5'-hydroxyl. In other embodiments, an RtcB ligase may be used, in which case the first adaptor should have a 5'-hydroxyl. In both cases, the 3' end of the first adaptor may be blocked so that it does not interfere with the ligation and/or subsequent steps.

As noted above, the eukaryotic tRNA ligase used in the method may minimally have a ligase domain and phosphodiester domains having an amino acid sequence that is at least 80% to the amino acid of the ligase domains phosphodiester domains of a wild type eukaryotic tRNA ligase. Such enzymes have been identified and characterized in yeast and plants, and are expected to be present in a number of other eukaryotes, e.g., mammals and archebacteria (see, e.g., Ramirez RNA 2008 14: 1737-45; Englert Nuc. Acids Res. 2005 33: 388-399; Sawaya J. Biol. Chem. 2003 278: 43928-43928; Apostol J. Biol. Chem. 1991 266: 7445-7455; Phizicky J. Biol. Chem. 1986 261: 2978-2986; Nandakumar Mol. Cell. 2008 31: 278-286; Sugahara RNA 2007 13: 671-681; and Schutz RNA 2010 16: 621-631). A eukaryotic tRNA ligase employed in a subject method may only have the ligase activity and cyclic phosphodiesterase activity of a wild type enzyme. The ligase domain is sufficient to catalyze ligation of the 5' terminus of a nucleic acid having a 5'-phosphate to the 3' terminus of a nucleic acid having a 3' terminus having a 2'-phosphate and a 3'-hydroxyl to produce a ligation product that contains a 2' phosphate at the site of ligation. The 2'-phosphate group may be removed by a 2'-phosphate group-specific specific phosphotransferase in the presence of $NAD^+$, or with a nonspecific alkaline phosphatase, if necessary (Culver J. Biol. Chem. 1997: 13203-13210; Schutz RNA 2010 16: 621-631). In particular embodiments, the ligase domain of the enzyme used may have an amino acid sequence that is at least 85%, at least 90%, at least 95% or up to 100% identical to the amino acid sequence of the ligase domain of a wild type eukayotic tRNA ligase. Likewise, the cyclic phosphodiesterase domain may be at least 85%, at least 90%, at least 95% or up to 100% identical to the amino acid sequence of the cyclic phosphodiesterase domain of a wild type eukayotic tRNA ligase. Since these enzymes are modular, then the enzyme used may have chimeric sequences from different species. For example, in one embodiment, the enzyme used may have: a) a ligase domain that is at least 80% identical to the ligase domain of a eukaryotic tRNA ligase from a first species and, b) a cyclic phosphodiesterase domain that is at least 80% identical to the cyclic phosphodiesterase domain of a eukaryotic tRNA ligase from a second species. Guidance for which amino acids to change in order to inactivate the kinase and/or cyclic phosphodiesterase activities of a eukaryotic tRNA ligase can be obtained from published material about those enzymes, as well as what is known about other kinases and cyclic phosphodiesterases. In particular cases, the ligation may be done in the presence or absence of ATP.

In alternative methods, an RtcB enzyme may be employed. In the *E. coli* genome and in the genomes of many other species, rtcB is in an operon with two other genes, rtcA and rtcR. RtcR is a transcriptional regulator and regulates the expression of rtcA and rtcB. RtcA is found in bacteria, archaea, and eukaryotes including humans (see, e.g., Genschik et al (J. Biol. Chem. 1998 273:25516-25526), Genschik et al (EMBO J. 1997 16:2955-2967) and Tanaka et al (RNA 2009 15:1865-1874)). RtcA is an RNA 3'-terminal phosphate cyclase that converts a 3'-phosphate at the end of an RNA molecule to a 2',3'-cyclic phosphodiester. The 2',3'-cyclic phosphodiester is a substrate of RtcB, whereas 3'-P is not. A phylogenetic analysis by Englert, supra, suggests that the last common ancestor of archaea and eukaryotes possessed an RtcB that functioned similarly to the *P. aerophilum* RtcB, and the conservation of RtcB implicates it as a eukaryotic 2',3'-cyclic phosphate RNA ligase. RtcB is absent in *Saccharomyces cerevisiae* and some plants, although yeast and plants have a structurally different RNA ligase that works through a distinct mechanism; there are no known orthologs of RtcB in these organisms.

In certain cases the enzyme used may be thermostable (i.e., capable of at least 50% of its original activity after heating to 70° C. for 10 minutes in its recommended reaction buffer) or heat sensitive (i.e., capable of less than 1% of its original activity after heating to 70° C. for 10 minutes in its recommended reaction buffer). Thermostable enzymes may be obtained from thermostable species, e.g., in thermophilic archaea or thermophilic bacteria. For example, the genes of the Rtc operon are present in *Pyrococcus furiosis* (which has an optimal growth temperature of 100° C.), *Archaeoglobus fulgidis* (which has an optimal growth temperature of 83° C.),

*Methanobacterium thermoautotrophicum* (which has an optimal growth temperature of 65-70° C.), and many other thermophilic archaea and bacteria, as described above. A 3'-OH RNA ligase that joins RNA fragments containing a 5'-PO and a 3'-OH has been identified in *Methanobacterium thermoautotrophicum* (MthRnl; Torchia et al, supra). These enzymes or their orthologs from other species may be employed in certain embodiments of the method.

The RtcB enzyme used in the method may be derived from a variety of species, including archaeal, bacterial and eukaryotic species. Exemplary archaeal species from which the enzyme may be obtained include, for example: *M. kandleri, M. thermautotrophicus, M. smithii, M. stadtmanae, M. jannashi, M. aeolicus, M. maripaludis, M. vannieli, A. fulgidus, M. labreanum, M. boonei, M. hungatei, M. marsngiri, M. palustris, M. thermophila, M. burtonii, M. barkeri, M. mazei, M. acetivorans, P. furiosus, P. abyssi, P. horikoshii, T. sibiricus, T. kodakarensis, T. gammatolerans, T. onnurineus, T. pendens, C. maquilingensis, P. calidifontis, P. arsenaticum, P. aerophilum, T. neutrophilus, P. islandicum, D. kamchatkensis, S. marinus, S. acidocaldarius, S. tokodaii, S. islandicus, M. sedula, S. solfataricus, I. hospitalus, A. pernix, H. butylicus, H. borinquense, H. turkenica, N. magadii, H. utahenis, N. pharaonis, H.* sp NRC-1, *H. lacusprofundi, N. equitans, T. acidophilum, T. volcanium, F. acidomarnus* and *P. torridus*. Sequences for these proteins have been deposited into NCBI's Genbank database by others.

Exemplary bacterial species from which an RtcB enzyme may be obtained include, for example: *D. radiodurans, C. aurantiacus, P.* sp TDR-2, *B. halodurans, M. xanthus, K. radiotolerans, A. aurescens, R. erythropolis, C. aurimucosum, S. cellulosum, M. xanthus, T. turnerae, D. dadantiis, E.* sp 638, *S. enterica, E. coli, P. aeruginosa, C. violaceum, R. pickettii, C. taiwanensis, V. paradoxus, P. naphthalenivorans, D. acidovorans, B. avium, X. campestris, S. maltophilia, D. aromatica, T.* sp MZ1T, *S. viridis, A. baumannii, A.* sp BH72, *H. chejuensis, J. denitrificans, B. faecium, N. farcinica, S. viridis, T. fusca, S. avermitilis, C. acidiphila, S. ruber, A. mirum, F. alni, M. aeruginosa, A. marina, N. punctiforme, A. variabilis, C. thalassium, B. bacteriovorus, L. sphaericus, l. welshimeri, D. hafniense, C. thermocellum, A. oremlandll, N. europea, T. maritima, T. thermophilus, A. aeolicus* and *K. olearia*. Sequences for these proteins have been deposited into NCBI's Genbank database by others.

Exemplary eukaryotic species from which an RtcB enzyme may be obtained include, for example: *C. merolae, A. anophagefferens, M.* sp. RCC299, *O. lucimarinus, C. intstinalis, B. malayi, C. elegans, S. purpuratus, B. floridae, G. gallus, T. guttata, D. rerio, N. vectensis, D. discoideum, T. annulata, P. falciparum, D. palex, N. vitripennis, A. mellifera, T. castaneum, A. pisum, D. melanogaster, A. gambiae,* and *T. equinum* as well as mammal, e.g., *M. domestica, M. mulatta, S. scrofu, E. caballus, R. norvegicus, O. anatinus, B. tarus, C. lupus, P. troglodytes* and *H. sapiens*. Sequences for these proteins have been deposited into NCBI's Genbank database by others.

The structure/function relationships of the *E. coli* RtcB is described in Tanaka, (supra) and the *P. aerophilum* RtcB is described in Englert (supra). The ligase activity of recombinant *P. aerophilum* RtcB may be metal ion ($Zn^2$) dependent, and mutagenesis of that protein implicated Cys100, His205, and His236 as residues that are at the active site. This work is an agreement with the crystal structure of the *P. horikoshii* protein (Okada, supra).

Given that the amino acid sequences for the same enzyme from several different species are known, the crystal structure of one protein is known, the active site is known at least two proteins have been characterized biochemically and activity assays are known, variants of a wild type enzyme may be designed and used. In particular embodiments, the enzyme used in the method may be naturally occurring (i.e., found in nature) or may be non-naturally occurring. Non-naturally occurring enzymes may have an amino acid sequence that is at least 50%, e.g., at least 60%, at least 70%, at least 80%, at least 90%, at least 95%, at least 98%, or at least 99% identical to a wild type enzyme.

For example, variants may be designed by aligning sequences from different species, and transferring amino acids residues that are at the same position (particularly conserved amino acids) but different from one sequence to another.

Further sequences may be identified by performing sequence comparisons, e.g., by BLAST searches, any of the sequences listed above with NCBI's sequence database. The method may be performed using as yet undiscovered orthologs of these emzymes. Other wild type sequences can be obtained by routine methods (e.g., by PCR or by hybridization, etc.).

As illustrated, in FIG. 2, this ligation step may be done by contacting the product RNA sample 12 with a 2',3'-cyclic phosphate-specific ligase 22 and the first adaptor 24 (which may be as short as a single nucleotide for some labeling methods), thereby producing a ligated sample containing ligation products 28 that contain the first adaptor. In certain applications, the first adaptor may: a) have a label, b) may have an affinity tag or c) may have a sequence for an RNA polymerase, as indicated by reference numeral 26.

In embodiments in which the first adaptor is labeled, the adaptor-ligated sample may be hybridized to an array of nucleic acid probes, and the array is read to obtain an estimate of the abundance of the targeted RNAs in the initial RNA sample. In particular embodiments, the array is read to obtain estimates of the abundance of a plurality of (i.e., at least 10, at least 100, at least 500, at least 1,000, at least 10,000, or at least 50,000 up to at least 100,000) different target RNAs in the initial RNA sample. The nucleic acid probes that are for detection of the target RNAs contain a sequence that is complementary to the target RNAs as well as, in particular embodiments, a sequence that is complementary to at least part of the adaptor sequence. In these embodiments, the method may further comprise: a) hybridizing the labeled RNA sample to an array; b) reading the array to provide results, and c) analyzing the results to obtain information on said initial sample.

Suitable labels include fluorescent dyes that include xanthene dyes, e.g. fluorescein and rhodamine dyes, such as fluorescein isothiocyanate (FITC), 6-carboxyfluorescein (commonly known by the abbreviations FAM and F),6-carboxy-2',4',7',4,7-hexachlorofluorescein (HEX), 6-carboxy-4',5'-dichloro-2', 7'-dimethoxyfluorescein (JOE or J), N,N,N', N'-tetramethyl-6-carboxyrhodamine (TAMRA or T), 6-carboxy-X-rhodamine (ROX or R), 5-carboxyrhodamine-6G ($R6G^5$ or $G^5$), 6-carboxyrhodamine-6G ($R6G^6$ or $G^6$), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. Specific fluorophores of interest that are commonly used in some applications include: pyrene, coumarin, diethylaminocoumarin, FAM, fluorescein chlorotriazinyl, R110, eosin, JOE, R6G, tetramethylrhodamine, TAMRA, lissamine, ROX, napthofluorescein, Texas red, napthofluorescein, Cy3, and Cy5, etc. Suitable distinguishable fluorescent label pairs useful in the subject methods include Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), and POPRO3 TOPRO3 (Molecular Probes, Eugene, Oreg.). Further suitable distinguishable detectable labels may be found in Kricka et al. (Ann Clin Biochem. 39:114-29, 2002). Labeled dinucleotides are known.

As mentioned above, the adaptor used in the ligation step may in certain embodiments contain an affinity tag. In these embodiments, the method may further comprise separating the adaptor-ligated fragments from the non-ligated fragments and uncleaved RNAs using the affinity tag. For example, if the affinity tag is a biotin moiety, the adaptor-ligated fragments can be separated from the other RNA using streptavidin or avidin beads, methods for the use of which are well known in the art. As such, the method may further comprise purifying the ligation products from other molecules in the ligated sample using said affinity tag.

This method provides an effective way for purifying target sequences from other sequences in the sample. The isolated sequences may be subjected to further analysis, e.g., converted into cDNA and sequenced or, alternatively, labeled and hybridized to an array. In certain cases, the RNA may by labeled by ligation to a labeled adaptor or by using the Universal Linkage System (ULS, KREATECH Diagnostics; van Gijlswijk et al Universal Linkage System: versatile nucleic acid labeling technique Expert Rev. Mol. Diagn. 2001 1:81-91). In brief, ULS labeling is based on the stable binding properties of platinum (II) to nucleic acids. The ULS molecule consists of a monofunctional platinum complex coupled to a detectable molecule of choice. Alternative methods may be used for labeling the RNA, for example, as set out in Ausubel, et al, (Short Protocols in Molecular Biology, 3rd ed., Wiley & Sons, 2002) and Sambrook, et al, (Molecular Cloning: A Laboratory Manual, Third Edition, (2001) Cold Spring Harbor, N.Y.).

Finally, in certain embodiments, the first adapter may contain a sequence for an RNA polymerase promoter. In these embodiments, the method may involve a) making double stranded cDNA from the product RNA sample using a primer that hybridizes with said first adaptor and a reverse transcriptase, and b) transcribing the cDNA using an RNA polymerase in the presence of labeled a rNTP, thereby making labeled RNA. Alternatively, the method may comprise: a) making cDNA from the product RNA sample using a primer that hybridizes with the first adaptor and a reverse transcriptase; b) adding a second adaptor to said cDNA at the opposite end to the first adaptor; c) amplifying the cDNA using primers that bind to the first and second adaptors. This cDNA may be sequenced or analyzed by some other means. These steps may be readily adapted from known protocols.

Figure 3:
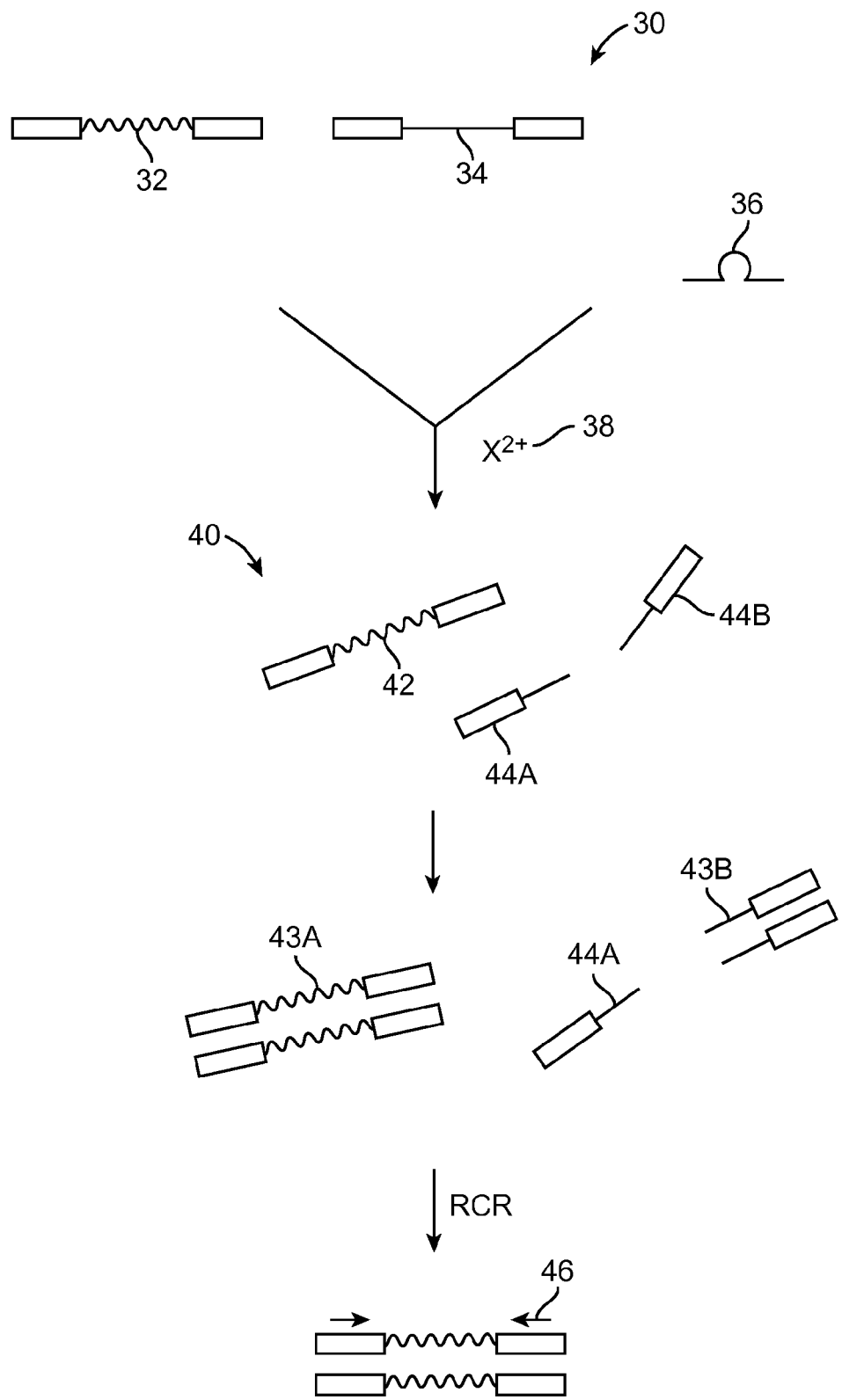
FIG. 3 schematically illustrates another embodiment of the method.

In an alternative embodiment illustrated in FIG. 3, the initial RNA sample 30 may comprises adaptor-ligated RNA molecules 32 and 34 that have both a 3' adaptor and a 5' adaptor (i.e., that have a 3' adaptor ligated at to their 3' ends and a 5' adaptor ligated to their 5' ends). The 3' and 5' adaptors may be different or the same. In these embodiments, only the uncleaved RNA molecules in the sample are amplifiable by PCR (after being converted to cDNA) and, as such, the method effectively provides another way of removing particular RNAs (e.g., abundant RNAs) from a sample. In these embodiments, the method may comprise, after the DNAzyme treatment, making cDNA using a primer that hybridizes with the 3' adaptor. cDNA copied from the uncleaved RNA molecules can be amplified using primers that are complementary to the 3' and 5' adaptor sequences. With reference to FIG. 3, the initial sample is contacted with a DNAzyme 36 and a divalent cation 38 to produce a product RNA sample 40 that comprises: a) uncleaved RNA molecules 42 and b) cleaved RNA fragments 44A and 44B that, as described above, contain a 2',3'-cyclic-phosphate and a 5' hydroxyl as the result of DNAzyme cleavage. The product RNA sample 40 is then reverse transcribed into cDNA 42A and 42B using a primer that hybridizes with the 3' adaptor, and the cDNA is subjected to PCR using primers that are complementary to (or have the same sequence as) the adaptors, to produce PCR product 46. Because only intact RNA molecules have both adaptor sequences (i.e., adaptor sequences at both the 3' and the 5' ends only the intact molecules are amplified. The amplified cDNA can be sequenced or labeled and hybridized to an array by any convenient means.

In one embodiment, the 3' and 5' adaptors contain sequences that are compatible with a next generation sequencing platform such as that of Illumina, SOLiD or Ion Torrent, such that the cDNA can be amplified with one set of primers and sequenced with a second set of primers, where both sets of primers hybridize with sequences provided by the 3' and 5' adaptors. In other words, the product generated by this method may be general compatible with one or more next-generation sequencing platforms. In certain embodiments, the products may be clonally amplified in vitro, e.g., using emulsion PCR or by bridge PCR, and then sequenced using, e.g., a reversible terminator method (Illumina and Helicos), by pyrosequencing (454) or by sequencing by ligation (SOLiD). Examples of such methods are described in the following references: Margulies et al (Genome sequencing in microfabricated high-density picoliter reactors". Nature 2005 437: 376-80); Ronaghi et al (Real-time DNA sequencing using detection of pyrophosphate release Analytical Biochemistry 1996 242: 84-9); Shendure (Accurate Multiplex Polony Sequencing of an Evolved Bacterial Genome Science 2005 309: 1728); Imelfort et al (De novo sequencing of plant genomes using second-generation technologies Brief Bioinform. 2009 10:609-18); Fox et al (Applications of ultra-high-throughput sequencing. Methods Mol. Biol. 2009; 553:79-108); Appleby et al (New technologies for ultra-high throughput genotyping in plants. Methods Mol. Biol. 2009; 513:19-39) and Morozova (Applications of next-generation sequencing technologies in functional genomics. Genomics. 2008 92:255-64), which are incorporated by reference for the general descriptions of the methods and the particular steps of the methods, including all starting products, reagents, and final products for each of the steps. The methods described above may be employed to investigate any genome, of known or unknown sequence, e.g., the genome of a plant (monocot or dicot), an animal such a vertebrate, e.g., a mammal (human, mouse, rat, etc), amphibian, reptile, fish, birds or invertebrate (such as an insect), or a microorganism such as a bacterium or yeast, etc.

Figure 4:
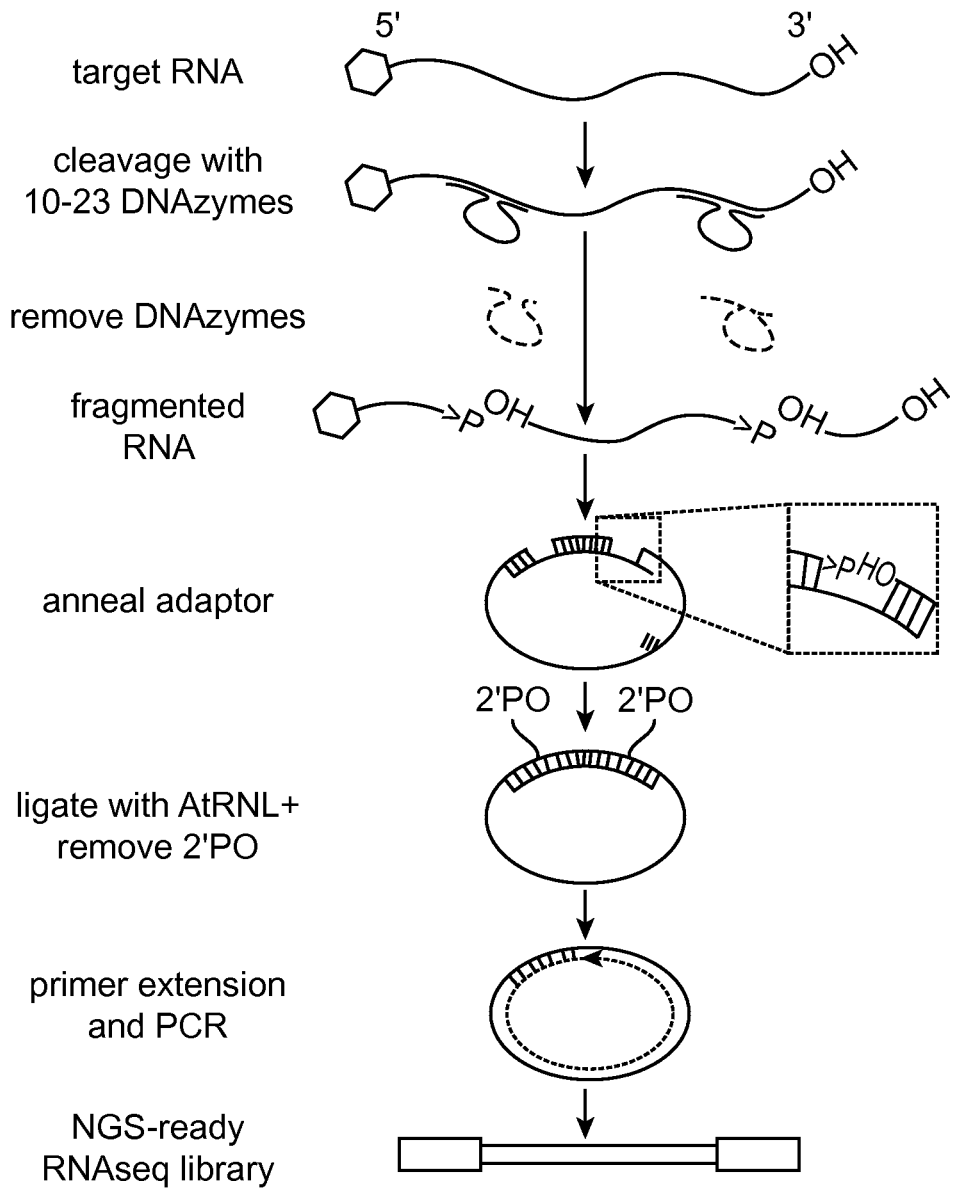
FIG. 4 schematically illustrates a further embodiment of the method.

In certain embodiments, the method may comprise contacting an initial RNA sample containing a population of different RNA molecules with a divalent cation and a first DNAzyme and a second DNAzyme, wherein said first and second DNAzymes both the cleave the same RNA molecule to produce an RNA product that has a defined sequence of nucleotides at its ends. This method may comprise ligating the ends of the RNA product to a single adaptor to produce a circular product molecule using the workflow outlined in Dahl et al (Nucl. Acids Res. 2005 33: e71) and U.S. Pat. No. 7,883,849, whch are incorporated by reference for all purposes, including oligonucleotide design parameters and reaction conditions). Certain aspects of this method are schematically illustrated in FIG. 4.

In the method of Dahl et al (Nucl. Acids Res. 2005 33: e71) and U.S. Pat. No. 7,883,849 restriction enzymes are used to clip genomic DNA in defined places, followed by making the DNA single-stranded and hybridizing the bridge probes of user-defined sequence to the two ends of one strand of genomic DNA, thus circularizing it and bringing the two cleaved ends of one DNA fragment into close apposition. A third probe that contains adaptor sequences that are read and utilized by next-generation sequencers (Illumina HiSeq, MiSeq, GAII, etc.) is hybridized to the single-stranded bridge, and a ligase joins the two bridge-splinted 'nicks' to close the circle. The second strand is synthesized by extension from the bridge around the circle, followed by PCR amplification using primers that bind to the adaptor sequences. Using the this technology, a genomic library can be constructed rapidly.

This disclosure also contemplates adapting the Dahl method by using DNAzymes to produce RNA molecules that have been cleaved in defined places, which is particularly useful in the production of RNA sequencing libraries. Instead of using DNA restriction endonucleases to initiate cleavage, 10-23 DNAzymes (which can be targeted to cleave virtually any sequence of RNA in a user-defined way) are used to create two breaks per RNA of interest, which leave 5'-OH and 2',3'-cyclic phosphate (denoted '>P') ends as a consequence of cleavage. As shown in FIG. 4, these ends can be splinted by a bridge oligonucleotide that contains a 'bottom' strand that hybridizes with sequences surrounding the breaks to tether a broken circle, and a 'top' strand (the shorter one in FIG. 4) containing ends that are compatible with the use of a eukaryotic tRNA ligase (RNL) which heals and seals the broken ends of RNA to the top adaptor sequence. The 2'PO tags can be removed, and a primer can be extended by reverse transcriptase to create a cDNA copy of the RNA of interest (dotted line in figure), followed by PCR. The linear product of the PCR contains the requisite 5' and 3' adaptors (black boxes) for sequencing.

This embodiment enables the production of user-defined RNA sequencing libraries considerably faster than the current approachs. Additionally, because this is a direct adaptor-ligation approach, RNA strand information is preserved.

Consistent with what is described above, also provided are compositions comprising a plurality of DNAzymes that are designed to cleave multiple target RNAs. In particular embodiments, the DNAzymes are $T_m$ matched. The composition may comprise additional reagents, e.g., total RNA, consistent with what is described above.

Kits

Also provided by the subject invention are kits for practicing the subject methods, as described above. The subject kits contain at least: a plurality of DNAzymes that are designed to cleave multiple target RNAs in a sample. The kit may optionally contain other components, for example: a labeled or affinity-tagged adaptor, 3' and 5' adaptors, T4 RNA ligase, reverse transcriptase, PCR reagents, labeled nucleotides or ribonucleotides, etc. The various components of the kit may be present in separate containers or certain compatible components may be precombined into a single container, as desired.

In addition to above-mentioned components, the subject kits may further include instructions for using the components of the kit to practice the subject methods, i.e., to instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

Utility

The methods described above may be employed to investigate the transcriptome of any organism, e.g., a plant (monocot or dicot), an animal such a vertebrate, e.g., a mammal (human, mouse, rat, etc), amphibian, reptile, fish, birds or invertebrate (such as an insect), or a microorganism such as a bacterium or yeast, etc.

The subject method may be employed in a variety of diagnostic, drug discovery, and research applications that include, but are not limited to: high throughput sequencing, genotyping, mutation detection, functional genomics, mapping and gene expression analysis. In particular embodiments, the method may be employed in the diagnosis or monitoring of a disease or condition (where the expression of particular RNAs provide a marker for the disease or condition), discovery of drug targets (where a particular RNA is differentially expressed in a disease or condition and may be targeted for drug therapy), drug screening (where the effects of a drug are monitored by assessing the level of an RNA), determining drug susceptibility (where drug susceptibility is associated with a particular profile of RNAs), basic research (where is it desirable to identify the presence and/or function of RNAs in a sample, or, in certain embodiments, the relative levels of a particular RNAs in two or more samples) and mutation detection, etc.

In certain embodiments, relative levels of RNAs in two or more different small RNA samples may be obtained using the above methods, and compared. In these embodiments, the results obtained from the above-described methods are usually normalized to the total amount of RNA in the sample or to control RNAs (e.g., constitutive RNAs), and compared. This may be done by comparing ratios, or by any other means. In particular embodiments, the RNA profiles of two or more different samples may be compared to identify RNAs that are associated with a particular disease or condition (e.g., an RNA that is induced by the disease or condition and therefore may be part of a signal transduction pathway implicated in that disease or condition).

The different samples may consist of an "experimental" sample, i.e., a sample of interest, and a "control" sample to which the experimental sample may be compared. In many embodiments, the different samples are pairs of cell types or fractions thereof, one cell type being a cell type of interest, e.g., an abnormal cell, and the other a control, e.g., normal, cell. If two fractions of cells are compared, the fractions are usually the same fraction from each of the two cells. In certain embodiments, however, two fractions of the same cell may be compared. Exemplary cell type pairs include, for example, cells isolated from a tissue biopsy (e.g., from a tissue having a disease such as colon, breast, prostate, lung, skin cancer, or infected with a pathogen etc.) and normal cells from the same tissue, usually from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells) may be employed. In another embodiment of the invention, the experimental material is cells susceptible to infection by a pathogen such as a virus, e.g., human immunodeficiency virus (HIV), etc., and the control material is cells resistant to infection by the pathogen. In another embodiment of the invention, the sample pair is represented by undifferentiated cells, e.g., stem cells, and differentiated cells. Two different developmental stages, e.g., embryo vs. non-embryo or young cells vs. old cells may also be compared.

Cells from yeast, plants and animals, such as fish, birds, reptiles, amphibians and mammals may be used in the subject methods. In certain embodiments, mammalian cells, i.e., cells from mice, rabbits, primates, or humans, or cultured derivatives thereof, may be used. Accordingly, among other things, the instant methods may be used to link the expression of certain genes to certain physiological events.

Embodiments

A method comprising: contacting an initial RNA sample containing a population of different RNA molecules with a divalent cation and a set of DNAzymes that are designed to cleave multiple target RNAs in said initial sample, thereby producing a product RNA sample that comprises: a) uncleaved RNA molecules and b) cleaved RNA fragments that contain a 2',3'-cyclic-phosphate and a 5' hydroxyl as the result of DNAzyme cleavage. Embodiment 2. The method of embodiment 1, wherein said DNAzymes are 10-23 DNAzymes. Embodiment 3. The method of any of the prior embodiments including embodiment 1, wherein contacting is done by cycling through denaturation and renaturation temperatures to maximize cleavage by said DNAzyme. Embodiment 4. The method of any of the prior embodiments including embodiment 1, wherein said set of DNAzymes comprises at least 100 different DNAzymes that specifically target different RNAs. Embodiment 5. The method of any of the prior embodiments including embodiment 1, further comprising ligating a first adaptor onto the 3' ends of at least some of said cleaved RNA fragments using a 2',3'-cyclic phosphate-specific RNA ligase, thereby producing a ligated sample comprising ligation products. Embodiment 6. The method of any of the prior embodiments including embodiment 5, wherein said first adaptor comprises a 5'-phosphate or 5'-hydroxyl and said ligase is a eukarytic tRNA ligase. Embodiment 7. The method of any of the prior embodiments including embodiment 5, wherein said first adaptor comprises a 5'-hydroxyl and said ligase is an RtcB ligase. Embodiment 8. The method of any of the prior embodiments including embodiment 5, wherein said first adaptor is labeled, and the method produces a labeled RNA sample. Embodiment 9. The method of any of any of the prior embodiments including embodiment 8, wherein said method further comprises: a) hybridizing said labeled RNA sample to an array; b) reading said array to provide results, and c) analyzing said results to obtain information on said initial sample. Embodiment 10. The method of any of the prior embodiments including embodiment 5, wherein the first adaptor comprises an RNA polymerase promoter and said method comprises: a) making double stranded cDNA from said product RNA sample using a primer that hybridizes with said first adaptor and a reverse transcriptase, and b) transcribing the cDNA using an RNA polymerase in the presence of labeled a rNTP, thereby making labeled RNA. Embodiment 11. The method of any of the prior embodiments including embodiment 5, wherein said method comprises: a) making cDNA from said product RNA sample using a primer that hybridizes with said first adaptor and a reverse transcriptase; b) adding a second adaptor to said cDNA at the opposite end to said first adaptor; c) amplifying said cDNA using primers that bind to said first adaptor and second adaptors. Embodiment 12. The method of any of the prior embodiments including embodiment 11, wherein further comprising sequencing said cDNA. Embodiment 13. The method of any of the prior embodiments including embodiment 5, wherein said first adaptor contains an affinity tag, and said method further comprises purifying said ligation products from other molecules in said ligated sample using said affinity tag. Embodiment 14. The method of any of the prior embodiments including embodiment 1, wherein said initial RNA sample comprises adaptor-ligated RNA molecules that have a 3' adaptor and a 5' adaptor. Embodiment 15. The method of any of the prior embodiments including embodiment 14, wherein said method comprises, after said contacting, making cDNA using a primer that hybridizes with said 3' adaptor. Embodiment 16. The method of any of the prior embodiments including embodiment 14, amplifying cDNA copied from said uncleaved RNA molecules using primers that are complementary to the 3' and 5' adaptors. Embodiment 17. The method of any of the prior embodiments including embodiment 16, wherein said method further comprises sequencing said cDNA. Embodiment 18. The method of any of the prior embodiments including embodiment 17, wherein said set of DNAzymes target abundant RNAs in said initial sample. Embodiment 19. A composition comprising a plurality of DNAzymes that are designed to cleave multiple target RNAs. Embodiment 20. The composition of embodiment 19, wherein said DNAzymes are melting temperature matched.

The invention claimed is:

1. A method comprising: contacting an initial RNA sample containing a population of different RNA molecules with a divalent cation and a set of DNAzymes that are designed to cleave multiple target RNAs in said initial sample, thereby producing a product RNA sample that comprises: a) uncleaved RNA molecules and b) cleaved RNA fragments that contain a 2',3'-cyclic-phosphate and a 5' hydroxyl as the result of DNAzyme cleavage; and ligating a first adaptor onto the 3' ends of at least some of said cleaved RNA fragments using a 2',3'-cyclic phosphate-specific RNA ligase, thereby producing a ligated sample comprising ligation products.

2. The method of claim 1, wherein said DNAzymes are 10-23 DNAzymes.

3. The method of claim 1, wherein contacting is done by cycling through denaturation and renaturation temperatures to maximize cleavage by said DNAzyme.

4. The method of claim 1, wherein said set of DNAzymes comprises at least 100 different DNAzymes that specifically target different RNAs.

5. The method of claim 1, wherein said first adaptor comprises a 5'-phosphate or 5'-hydroxyl and said ligase is a eukaryotic tRNA ligase.

6. The method of claim 1, wherein said first adaptor comprises a 5'-hydroxyl and said ligase is an RtcB ligase.

7. The method of claim 1, wherein said first adaptor is labeled, and the method produces a labeled RNA sample.

8. The method of claim 7, wherein said method further comprises: a) hybridizing said labeled RNA sample to an array; b) reading said array to provide results, and c) analyzing said results to obtain information on said initial sample.

9. The method of claim 1, wherein the first adaptor comprises an RNA polymerase promoter and said method comprises: a) making double stranded cDNA from said product RNA sample using a primer that hybridizes with said first adaptor and a reverse transcriptase, and b) transcribing the cDNA using an RNA polymerase in the presence of labeled a rNTP, thereby making labeled RNA.

10. The method of claim 1, wherein said method comprises: a) making cDNA from said product RNA sample using a primer that hybridizes with said first adaptor and a reverse transcriptase; b) adding a second adaptor to said cDNA at the opposite end to said first adaptor; c) amplifying said cDNA using primers that bind to said first adaptor and second adaptors.

11. The method of claim 10, wherein further comprising sequencing said cDNA.

12. The method of claim 1, wherein said first adaptor contains an affinity tag, and said method further comprises purifying said ligation products from other molecules in said ligated sample using said affinity tag.

13. A method comprising:

contacting an initial RNA sample comprising a population of RNA molecules that have a 3' adaptor and a 5' adaptor with a divalent cation and a set of DNAzymes that are designed to cleave multiple target RNAs in said initial sample, thereby producing a product RNA sample that comprises: a) uncleaved RNA molecules and b) cleaved RNA fragments that contain a 2',3'-cyclic-phosphate and a 5' hydroxyl as the result of DNAzyme cleavage.

14. The method of claim 13, wherein said method comprises, after said contacting, making cDNA using a primer that hybridizes with said 3' adaptor.

15. The method of any of claim 13, further comprising amplifying cDNA copied from said uncleaved RNA molecules using primers that are complementary to the 3' and 5' adaptors.

16. The method of claim 15, wherein said method further comprises sequencing said cDNA.

17. A method comprising: contacting an initial RNA sample containing a population of different RNA molecules with a divalent cation and a set of DNAzymes that are designed to cleave multiple target RNAs in said initial sample to produce an RNA sample that comprises: a) uncleaved RNA molecules and b) cleaved RNA fragments that contain a 2',3'-cyclic-phosphate and a 5' hydroxyl as the result of DNAzyme cleavage, wherein the set of DNAzymes comprises a first DNAzyme and a second DNAzyme that both the cleave the same RNA molecule to produce an RNA product that has a defined sequence of nucleotides at its ends; and ligating the ends of said RNA product to an adaptor to produce a circular product molecule.

* * * * *

UNITED STATES PATENT AND TRADEMARK OFFICE
CERTIFICATE OF CORRECTION

| | | |
|---|---|---|
| PATENT NO. | : 8,815,782 B2 | Page 1 of 1 |
| APPLICATION NO. | : 13/666752 | |
| DATED | : August 26, 2014 | |
| INVENTOR(S) | : Gusti Zeiner et al. | |

It is certified that error appears in the above-identified patent and that said Letters Patent is hereby corrected as shown below:

In the Claims

In column 22, line 30, Claim 15, delete "of any of" and insert -- of --, therefor.

Signed and Sealed this
Thirty-first Day of March, 2015

Michelle K. Lee
*Director of the United States Patent and Trademark Office*